(12) United States Patent
Furuta

(10) Patent No.: US 9,854,960 B2
(45) Date of Patent: Jan. 2, 2018

(54) ILLUMINATION DEVICE

(71) Applicant: OLYMPUS CORPORATION, Tokyo (JP)

(72) Inventor: Koichiro Furuta, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 28 days.

(21) Appl. No.: 14/973,056

(22) Filed: Dec. 17, 2015

(65) Prior Publication Data

US 2016/0106306 A1 Apr. 21, 2016

Related U.S. Application Data

(63) Continuation of application No. PCT/JP2014/066789, filed on Jun. 25, 2014.

(30) Foreign Application Priority Data

Jul. 9, 2013 (JP) .................................. 2013-143681

(51) Int. Cl.
*A61B 1/07* (2006.01)
*A61B 1/06* (2006.01)
(Continued)

(52) U.S. Cl.
CPC ........ *A61B 1/0615* (2013.01); *A61B 1/00096* (2013.01); *A61B 1/00163* (2013.01);
(Continued)

(58) Field of Classification Search
CPC .............. A61B 1/0615; A61B 1/00096; A61B 1/00163; A61B 1/0623; A61B 1/0684;
(Continued)

(56) References Cited

U.S. PATENT DOCUMENTS

2008/0242935 A1 10/2008 Inoue
2011/0184244 A1 7/2011 Kagaya et al.
(Continued)

FOREIGN PATENT DOCUMENTS

JP H11-76148 A 3/1999
JP 2004-329700 11/2004
(Continued)

OTHER PUBLICATIONS

International Search Report, dated Sep. 22, 2014, issued in corresponding International Application No. PCT/JP2014/066789.

*Primary Examiner* — Y M. Lee
(74) *Attorney, Agent, or Firm* — Andrews Kurth Kenyon LLP

(57) ABSTRACT

An illumination device includes a light output unit having an output end; an optical member that is disposed in a circumferential direction centered on a predetermined axis and that receives illumination light output from the output end and outputs the illumination light from a surface thereof; and a reflective layer that is provided adjacent to a surface of the optical member at an inner side in a radial direction and that reflects the illumination light outward in the radial direction. The optical member includes, in order from one end in a direction along the axis, a light guide layer and a diffusion layer. The light guide layer receives the illumination light from the output end in the direction along the axis and guides the illumination light. The diffusion layer receives the illumination light from the light guide layer and guides the illumination light while diffusing the illumination light.

15 Claims, 6 Drawing Sheets

(51) Int. Cl.
*A61B 1/00* (2006.01)
*G02B 23/24* (2006.01)

(52) U.S. Cl.
CPC .......... *A61B 1/0623* (2013.01); *A61B 1/0684* (2013.01); *A61B 1/07* (2013.01); *G02B 23/2461* (2013.01); *G02B 23/2469* (2013.01)

(58) Field of Classification Search
CPC ..... A61B 1/07; A61B 1/00165; A61B 1/0607; A61B 1/0646; A61B 1/06; G02B 23/2461; G02B 23/26; G02B 23/2469
See application file for complete search history.

(56) References Cited

U.S. PATENT DOCUMENTS

2012/0051693 A1   3/2012  Yoshida et al.
2013/0287380 A1* 10/2013  Thursby .............. E21B 47/0002
                                                            396/19

FOREIGN PATENT DOCUMENTS

| JP | 2008-237790 A | 10/2008 | |
|----|---------------|---------|--|
| JP | 2010129282 A * | 6/2010 | ............... F21K 9/00 |
| JP | 2011-147757 A | 8/2011 | |
| JP | 2011-152371 A | 8/2011 | |
| JP | 2012-50607 A | 3/2012 | |
| JP | 2012-55342 A | 3/2012 | |

* cited by examiner

ILLUMINATION DEVICE

CROSS-REFERENCE TO RELATED APPLICATIONS

This is a continuation of International Application PCT/JP2014/066789, with an international filing date of Jun. 25, 2014, which is hereby incorporated by reference herein in its entirety. This application claims the benefit of Japanese Patent Application No. 2013-143681, filed on Jul. 9, 2013, the content of which is incorporated herein by reference.

TECHNICAL FIELD

The present invention relates to illumination devices, and particularly to an illumination device for use with endoscopes having viewing angles of 180° or more.

BACKGROUND ART

There is a known endoscope that has a wide viewing angle, i.e., 180° or more, and that allows simultaneous observation of forward, side, and even backward fields of view (see, for example, PTL 1 below). For example, if an endoscope having viewing angle of 180° or more is used in the large intestine, where numerous folds are found, the back side of a fold can be observed without changing the orientation of the distal end of the endoscope by a large amount, which allows the user to manipulate the endoscope more easily and to find an affected area more reliably. The endoscope in PTL 1 has, at the distal end thereof, an illumination device including two light guides and illuminates forward and side fields of view with different light guides to illuminate a wide field of view in its entirety.

Endoscopes have various components concentrated at the tips thereof, including image-capturing optical systems for capturing images of subjects, channels for surgical instruments, nozzles for lens cleaning, and mechanisms for bending bending sections thereof. Accordingly, there is a need for an illumination device that can be installed in a thin endoscope within the minimum possible space in the radial direction. The illumination device in PTL 1 includes a plurality of light guides arranged side-by-side in the radial direction in the surrounding part of the image-capturing optical system, and the distal end of the light guide for side illumination is bent in the radial direction of the endoscope to achieve side illumination. This requires a large installation space in the radial direction of the endoscope and thus results in a large increase in the tip diameter of the endoscope.

CITATION LIST

Patent Literature

{PTL 1}
Japanese Unexamined Patent Application, Publication No. 2004-329700

SUMMARY OF INVENTION

A first aspect of the present invention is an illumination device including a light output unit having an output end that outputs illumination light; an optical member that is disposed in a circumferential direction centered on a predetermined axis and that receives the illumination light from the output end and outputs the illumination light from a surface thereof; and a reflective layer that is provided adjacent to a surface of the optical member at an inner side in a radial direction and that reflects the illumination light outward in the radial direction. The optical member comprises, in order from one end in a direction along the predetermined axis, a light guide layer and a diffusion layer. The light guide layer receives the illumination light from the output end in the direction along the predetermined axis and guides the illumination light. The diffusion layer receives the illumination light from the light guide layer and guides the illumination light while diffusing the illumination light.

A second aspect of the present invention is an illumination device including a light output unit having an output end that outputs illumination light; an optical member that is disposed in a circumferential direction centered on a predetermined axis and that receives the illumination light from the output end and outputs the illumination light from a surface thereof; and a reflective layer that is provided inside a surface of the optical member at an inner side in a radial direction and that reflects the illumination light outward in the radial direction. The optical member includes, in order from one end in a direction along the predetermined axis, a light guide layer and a diffusion layer. The light guide layer receives the illumination light from the output end in the direction along the predetermined axis and guides the illumination light. The diffusion layer receives the illumination light from the light guide layer and guides the illumination light while diffusing the illumination light.

DESCRIPTION OF EMBODIMENTS

First Embodiment

An illumination device 100 according to a first embodiment of the present invention will be described below with reference to FIGS. 1A to 4.

Figure 1A:
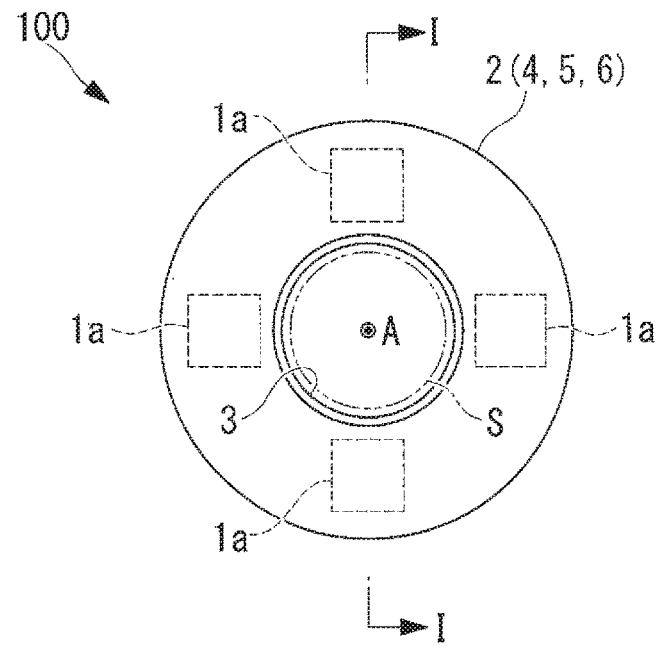
FIG. 1A is a front view showing the overall configuration of an illumination device according to a first embodiment of the present invention.
Figure 1B:
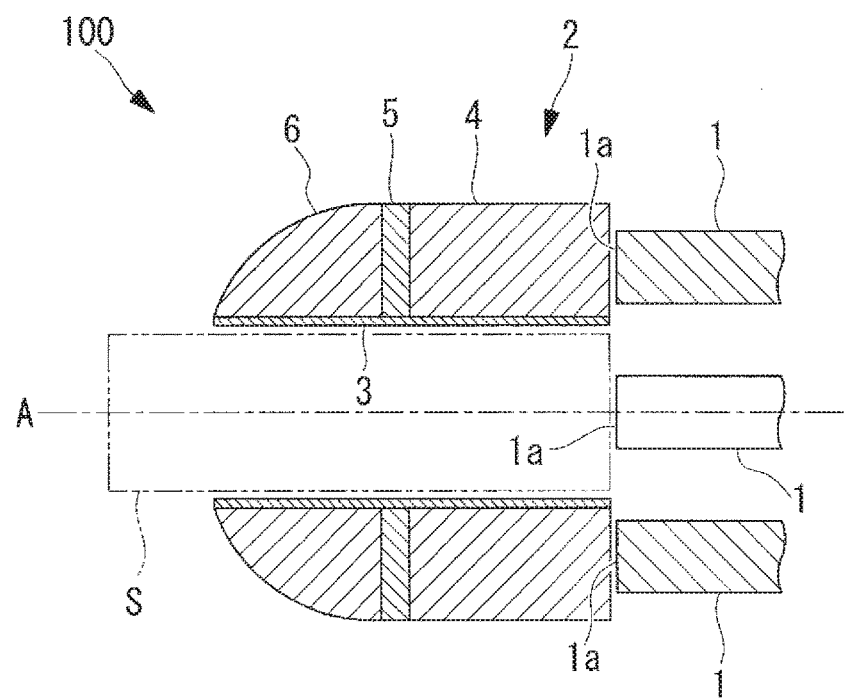
FIG. 1B is a longitudinal sectional view, taken along line I-I, of the illumination device in FIG. 1A.

As shown in FIGS. 1A and 1B, the distal-end portion of the illumination device 100 according to this embodiment (i.e., a portion composed of an optical member 2 and a reflective layer 3, described later) has a cylindrical structure and is exposed to the outside so as to circumferentially surround an image-capturing optical system provided at the distal end of an endoscope. In the same figures, the space S enclosed by the two-dot chain line represents the space where the image-capturing optical system is disposed, and the axis A represents the observation optical axis of the image-capturing optical system. In particular, the illumination device 100 according to this embodiment is designed for endoscopes including image-capturing optical systems having viewing angles of 180° or more and capable of simultaneously capturing images of fields of view forward (in the drawings, in the direction from right to left) and sideward of the observation optical axis A.

Specifically, as shown in FIGS. 1A and 1B, the illumination device 100 includes light output units 1 having output ends 1a that output illumination light, a substantially cylindrical optical member 2 that is provided at the distal ends of the light output units 1 and that receives the illumination light from the output ends 1a, guides the illumination light while diffusing it, and outputs the illumination light from a surface thereof, and a reflective layer 3 provided on the inner circumferential surface of the optical member 2.

The light output units 1 are, for example, fiber bundles disposed inside the endoscope. The proximal ends of the fiber bundles are connected to a light source unit (not shown) disposed outside the endoscope, and illumination light supplied from the light source unit is guided through the fiber bundles and is output from the distal ends or the fiber bundles, i.e., from the output ends 1a. The output ends 1a are located opposite the proximal-end surface of the optical member 2 in sufficient proximity thereto and direct the illumination light into a light guide layer 4 (described later) located in the proximal-end portion of the optical member 2.

The color of the illumination light may be selected, as appropriate, depending on the application, preferably white for normal observation of subjects. For special light observation such as narrow-band imaging (NBI) and fluoroscopy, the illumination light may be narrow-band light, i.e., light having its emission spectrum only in a particular wavelength band.

Figure 2:
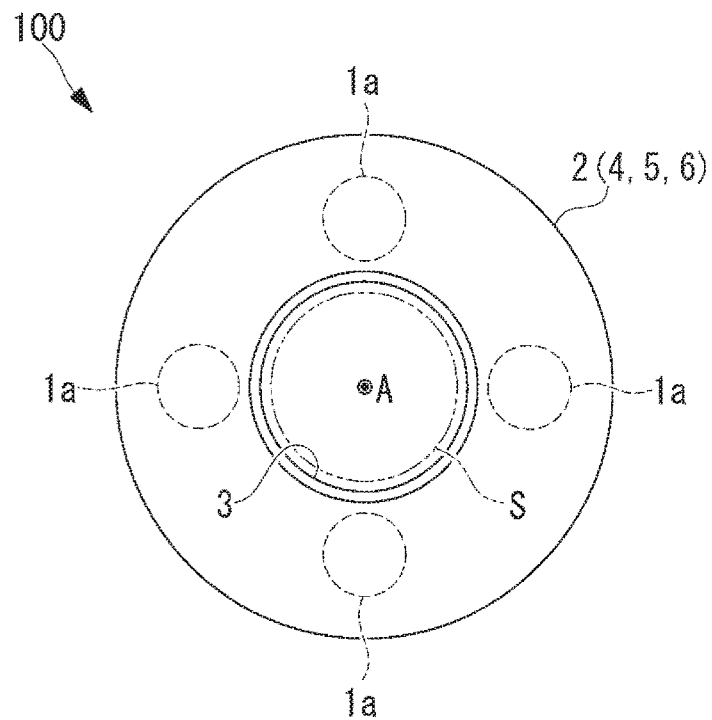
FIG. 2 is a front view of the illumination device, showing a modification of the shape of the output ends of the light output units in FIGS. 1A and 1B.
Figure 3:
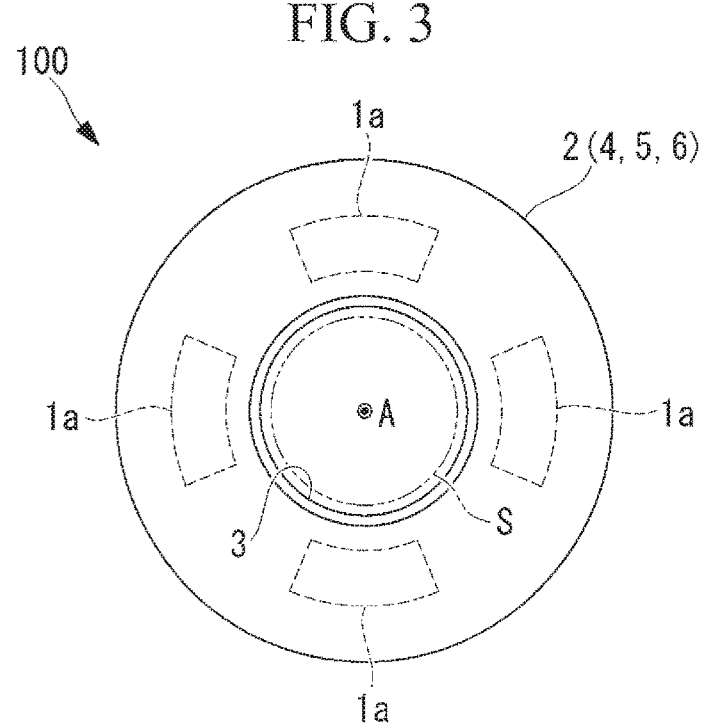
FIG. 3 is a front view of the illumination device, showing another modification of the shape of the output ends of the light output units in FIGS. 1A and 1B.

Although FIGS. 1A and 1B illustrate four light output units 1 arranged at regular intervals on a circumference centered on the observation optical axis A, the arrangement and number of light output units 1 may be changed, as appropriate. The light output units 1 may be, for example, small solid-state light sources such as LEDs and lasers, rather than fiber bundles. The shape of the output ends 1a may also be changed, as appropriate. As shown in FIGS. 2 and 3, the output ends 1a may be circular or annular-sector-shaped, and they may also have other shapes, including ovals and polygons other than rectangles. This improves the design flexibility of the light output unit.

The optical member 2 is disposed such that the central axis thereof (predetermined axis) is substantially in line with the observation optical axis (predetermined axis) A. A typical image-capturing optical system installed in the endoscope includes a plurality of lenses arranged in line along the observation optical axis A and a cylindrical frame holding the plurality of lenses inside. The optical member 2 is disposed around the outer circumferential surface of the frame.

The optical member 2 has a layered structure in which three layers 4, 5, and 6 are stacked in the longitudinal direction. Specifically, the optical member 2 includes a first light guide layer 4 located at the proximal end thereof, a second light guide layer 6 located at the distal end thereof, and a diffusion layer 5 located between the first light guide layer 4 and the second light guide layer 6. The adjacent end surfaces of these layers 4, 5, and 6 are joined to each other so that the illumination light can travel between the first light guide layer 4 and the diffusion layer 5 and between the diffusion layer 5 and the second light guide layer 6.

The first light guide layer 4 and the second light guide layer 6 are made of a light guide material through which the illumination light propagates. Examples of light guide materials include plastic materials such as acrylic and ZEONOR.

The diffusion layer 5 contain a same light guide material as the light guide material that forms the light guide layers 4 and 6 and a diffusion material that diffuses the illumination light. The diffusion material is dispersed and supported at substantially uniform density in the light guide material, which serves as a matrix. Examples of diffusion materials include titanium oxide.

Figure 4:
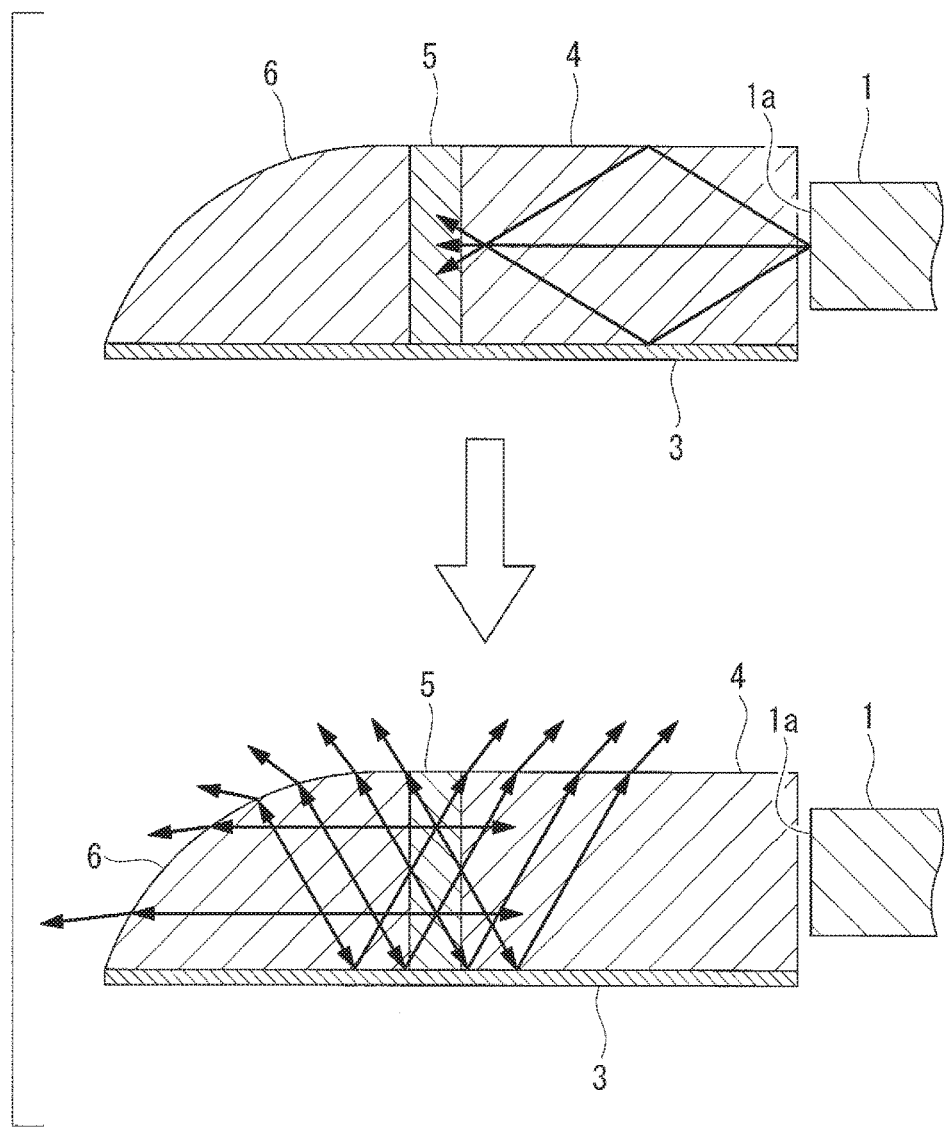
FIG. 4 illustrates the behavior of rays in the optical member in FIGS. 1A and 1B.

As shown in FIG. 4, the illumination light entering the proximal-end surface of the first light guide layer 4 is guided to the diffusion layer 5 along the observation optical axis A (see the upper part of FIG. 4). The illumination light is output as diffused rays from the output ends 1a; therefore, some rays are totally reflected by the surface of the first light guide layer 4.

While the illumination light entering the diffusion layer 5 is guided through the diffusion layer 5, the illumination light is substantially isotropically diffused by repeated refraction due to the difference in refractive index between the light guide material and the diffusion material and is thereby converted into substantially isotropically scattered light (see the lower part of FIG. 4). A portion of the illumination light that has been converted into substantially isotropically scattered light is output from the surface of the diffusion layer 5. The other portion of the illumination light enters the first light guide layer 4 or the second light guide layer 6 and is output from the surface of the first light guide layer 4 or the second light guide layer 6. Nearly all of the illumination light is output to the outside from the surfaces of the light guide layers 4 and 6 and the diffusion layer 5 that are exposed to the outside, i.e., the distal-end surface and the outer circumferential surface, under the reflection effect of the reflective layer 3, described later. Thus, the illumination light output toward the front with respect to the observation optical axis A from the distal-end surface of the second light guide layer 6 mainly illuminates the forward field of view of the observation optical system, whereas the illumination light output in the radial directions with respect to the observation optical axis A from the outer circumferential surfaces of the light guide layers 4 and 6 and the diffusion layer 5 mainly illuminates the side field of view of the observation optical system over the entire circumference thereof.

The distal-end surface of the optical member 2 has a conical shape that is smoothly continuous with the outer circumferential surface and that becomes gradually narrower toward the distal end, preferably a round conical shape. This allows the illumination light output from the distal-end surface and the outer circumferential surface to have uniform intensity at each angle and thus allows a wide field of view to be illuminated with uniform brightness at each position, thus providing good illumination performance.

The reflective layer 3 has a high reflectance for the illumination light and is provided inside the inner circumferential surface of the optical member 2 in the radial direction and adjacent to the inner circumferential surface of the optical member 2. The reflective layer 3 may be a sheet or pipe fixed to the inner circumferential surface of the optical member 2. The reflective layer 3 may be adjacent to the optical member 2 with an air layer therebetween or may be fixed to the optical member 2 with an optical adhesive having substantially the same refractive index as the optical member 2. Alternatively, the reflective layer 3 may be a reflective film formed on the inner circumferential surface of the optical member 2. The illumination light output from the inner circumferential surface of the optical member 2 is reflected back into the optical member 2 by the reflective layer 3; thus, nearly all of the illumination light entering the optical member 2 along the observation optical axis A is output from the distal-end surface and outer circumferential surface of the optical member 2 and contributes to the illumination of the forward and side fields of view. This provides high illumination efficiency.

The operation of the thus-configured illumination device 100 will now be described.

In the illumination device 100 according to this embodiment, the illumination light directed from the output ends 1a of the light output units 1 into the first light guide layer 4 of the optical member 2 enters the diffusion layer 5 located at the distal end of the light guide layer 4 and is guided through the diffusion layer 5 while being diffused in various directions. Some of the rays contained in the illumination light are output from the outer circumferential surface of the diffusion layer 5. Other rays contained in the illumination light enter the adjacent first light guide layer 4 or second light guide layer 6 and are output to the outside from the outer circumferential surface of the first light guide layer 4 or the distal-end surface or outer circumferential surface of the second light guide layer 6. The rays output from the inner circumferential surfaces of the layers 4, 5, and 6 are reflected back into the layers 4, 5, and 6 by the reflective layer 3 and are repeatedly diffused by the diffusion layer 5 and reflected by the reflective layer 3 until they are output from the outer surface of the optical member 2. In this way, the illumination light directed from the light output units 1 into the optical member 2 can simultaneously illuminate the forward and side fields of view of the observation optical system with sufficient brightness and little intensity loss.

The illumination light that has been converted into isotropically scattered light by nearly complete diffusion (Lambertian scattering) in the diffusion layer 5 is output in various directions from the distal-end surface or outer circumferential surface of the optical member 2. Since the distal-end surface and the outer circumferential surface of the optical member 2 are smoothly continuous in shape, there is no discontinuous change in brightness between the illumination light output from the distal-end surface and the illumination light output from the outer circumferential surface. This allows effective illumination with uniform brightness over a wide angular range, i.e., 180° or more.

In this case, the illumination device 100 according to this embodiment is a cylindrical device disposed in a thin space around the image-capturing optical system installed in the endoscope so as to be coaxial with the image-capturing optical system and has a layered structure with a sufficiently small size in the radial direction of the endoscope. The illumination device 100 can thus be built into the distal end of the endoscope with little increase in the tip diameter of the endoscope. Specifically, the illumination device 100 built into the distal end of the endoscope increases the tip diameter of the endoscope only by the thickness of the cylindrical optical member 2 and the reflective layer 3. The illumination device 100 is therefore advantageous in that it is suitable for use with than endoscopes.

The illumination light is also diffused backward (in the drawings, in the direction from left to right) with respect to the observation optical axis A in the diffusion layer 5. Specifically, a portion of the illumination light diffused by the diffusion layer 5 is output from the proximal-end surface of the optical member 2, which results in a loss in intensity of the illumination light. According to this embodiment, the first light guide layer 4, which has no diffusion effect on the illumination light, is disposed in the proximal-end portion where the illumination light is directed from the output ends 1a, and the diffusion layer 5 is disposed at a position away from the proximal-end surface of the optical member 2. This is advantageous in reducing the illumination light output from the optical member 2 backward with respect to the observation optical axis A and thereby achieving a higher illumination efficiency.

Although the optical member 2 in this embodiment has the two light guide layers 4 and 6 at both ends of the diffusion layer 5, the optical member 2 may include at least the light guide layer 4 in the proximal-end portion adjacent to the output ends 1a; that is it may have a double-layer structure including the light guide layer 4 and the diffusion layer 5.

Although the light guide layers 4 and 6 illustrated in this embodiment have no diffusion effect on the illumination light and allow the illumination light to travel in a straight line, the light guide layers 4 and 6 may contain a diffusion material as described above and may have a diffusion effect on the illumination light. However, the diffusion effect of the light guide layers 4 and 6 is made sufficiently weaker than that of the diffusion layer 5 to sufficiently reduce the illumination light output from the proximal-end of the optical member 2 by adjusting the density of the diffusion material.

Second Embodiment

An illumination device 200 according to a second embodiment of the present invention will now be described with reference to FIGS. 5 and 6. In this embodiment, the elements that differ from those of the first embodiment described above are mainly described, whereas the same elements as in the first embodiment are labeled with the same reference signs and are not described.

Figure 5:
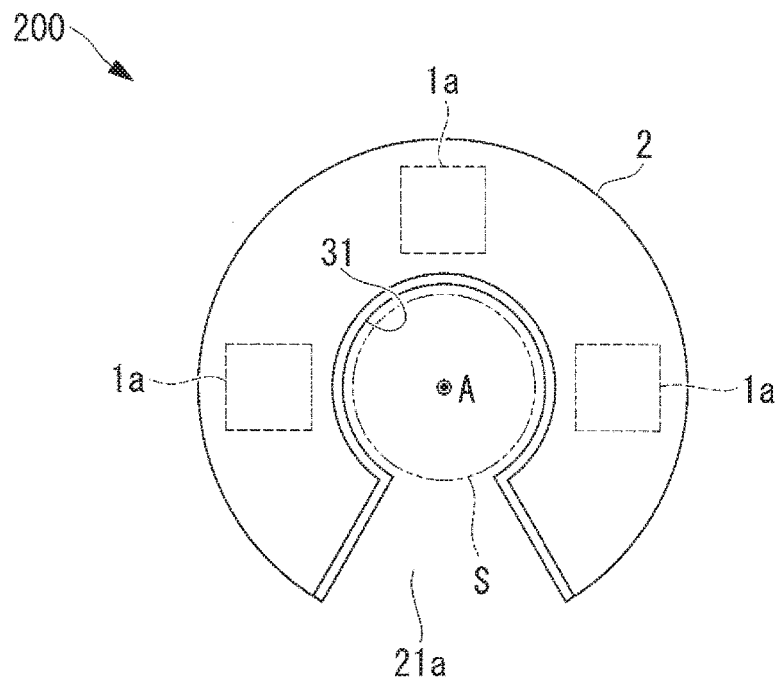
FIG. 5 is a front view showing the overall configuration of an illumination device according to a second embodiment of the present invention.
Figure 6:
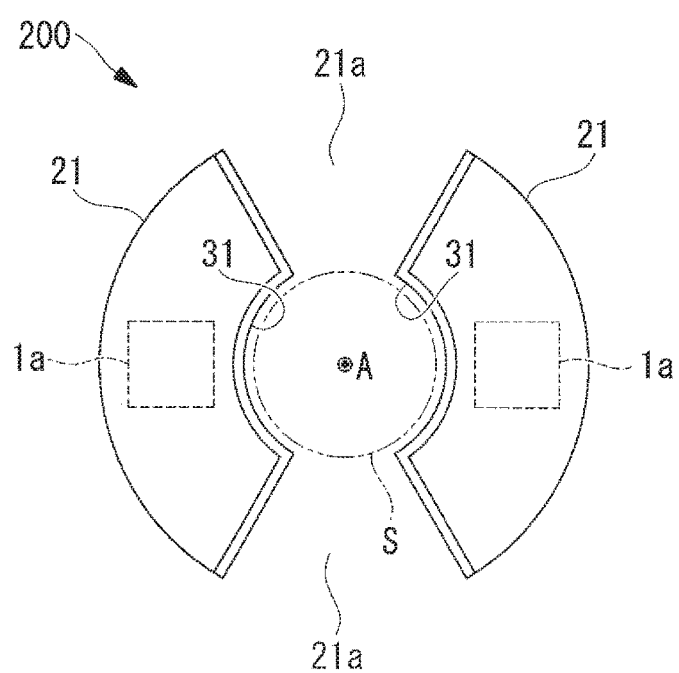
FIG. 6 is a front view of the illumination device, showing a modification of the optical member in FIG. 5.

As shown in FIG. 5, the illumination device 200 according to this embodiment differs from the illumination device 100 according to the first embodiment mainly in that the illumination device 200 includes an optical member 21 having an approximately C-shaped transverse cross-section formed by removing a portion extending in the circumferential direction, rather than the optical member 2 extending over the entire circumference thereof.

A cutout 21a formed by removing, in the longitudinal direction, a portion of the optical member 21 extending in the circumferential direction has an annular-sector-shaped transverse cross-section. The remaining configuration and operation of the optical member 21 are similar to those of the optical member 2 in the first embodiment.

A reflective layer 31 is provided on the inner circumferential surface of the optical member 21, as the reflective layer 3 is in the first embodiment, to reflect the illumination light output from the inner circumferential surface back into the optical member 21. Preferably, the reflective layer 31 is also provided on the sectional surfaces of the optical member 21 exposed in the cutout 21a to reflect the illumination light output from the sectional surfaces back into the optical member 21. The remaining configuration and operation of the reflective layer 31 are similar to those of the reflective layer 3 in the first embodiment.

Various components are disposed around the image-capturing optical system for design reasons. The illumination device 200 according to this embodiment allows such components to be installed in the space formed by the cutout 21a, which is advantageous in providing a more versatile structure. Another advantage is that, as in the first embodiment, the illumination device 200 allows effective and efficient illumination over a wide angular range, i.e., 180° or more, and is suitable for use with thin endoscopes.

In this embodiment, the shape and number of cutouts 21a may be changed, as appropriate. For example, the optical member 21 may be divided into a plurality of optical members 21 in the circumferential direction by forming a plurality of cutouts 21a in the circumferential direction such that the plurality or optical members 21 are arranged in the circumferential direction. In this case, each optical member 21 is a pillar member having a substantially horseshoe-shaped transverse cross-section perpendicular to the observation optical axis A and a side surface curved about the observation optical axis A at the inner side in the radial direction. FIG. 6 illustrates an example where the optical member 21 is divided into two members by forming two cutouts 21a in the circumferential direction.

As shown in FIGS. 2 and 3, the output ends 1a of the light output units 1 in this embodiment may have shapes other than rectangles.

The optical member 21 in this embodiment may have a double-layer structure including the first light guide layer 4 and the diffusion layer 5.

The light guide layers 4 and 6 in this embodiment may have a sufficiently weaker diffusion effect on the illumination light than the diffusion layer 5 does.

Third Embodiment

An illumination device 300 according to a third embodiment of the present invention will now be described with reference to FIGS. 7A to 8B. In this embodiment, the elements that differ from those of the first and second embodiments described above are mainly described, whereas the same elements as in the first and second embodiments are labeled with the same reference signs and are not described.

Figure 7A:
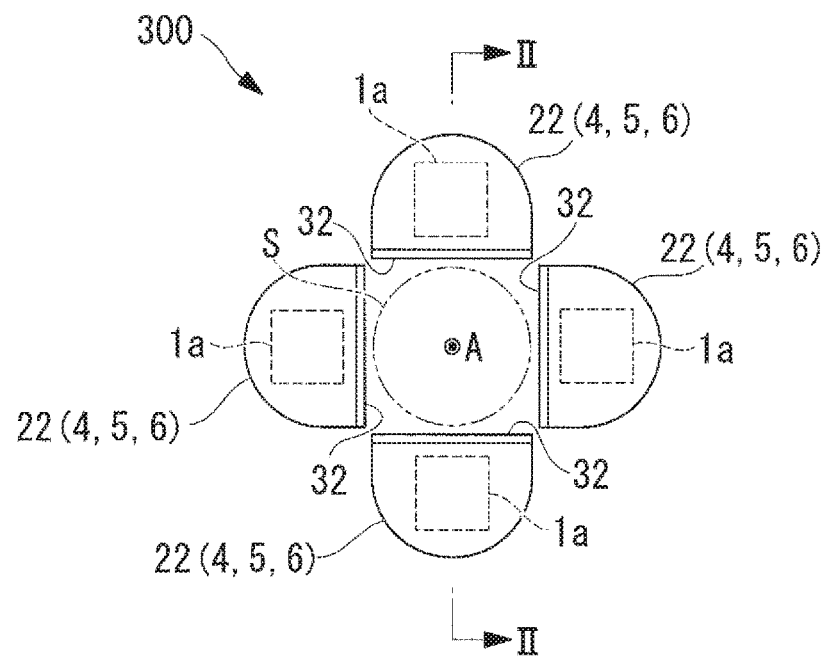
FIG. 7A is a front view showing the overall configuration of an illumination device according to a third embodiment of the present invention.
Figure 7B:
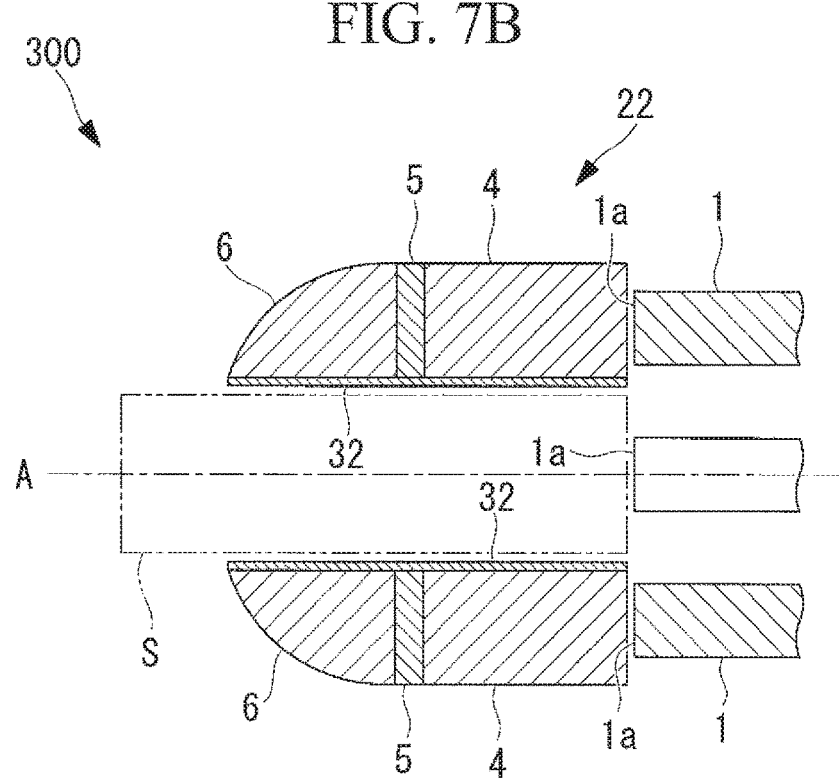
FIG. 7B is a longitudinal sectional view, taken along line II-II, of the illumination device in FIG. 7A.

As shown in FIGS. 7A and 7B, the illumination device 300 according to this embodiment differs from the illumination devices 100 and 200 according to the first and second embodiments mainly in that the illumination device 300 includes a plurality of (in this example, four) optical members 22 arranged substantially at regular intervals in the circumferential direction centered on the observation optical axis A, rather than the cylindrical optical members 2 and 21, and that the illumination device 300 includes four units each composed of an optical member 22, a reflective layer 32, and a light output unit 1.

Each optical member 22 is a substantially semicircular pillar member having a flat side surface at the inner side in the radial direction and a curved side surface at the outer side in the radial direction. The remaining configuration and operation of the optical members 22 are similar to those of the optical member 2 in the first embodiment.

The reflective layers 32 are provided on the flat side surfaces of the optical members 22 and have a flat shape. The remaining configuration and operation of the reflective layers 32 are similar to those of the reflective layer 3 in the first embodiment.

The thus-configured illumination device 300 according to this embodiment, which includes the four separate optical members 22, is advantageous in that the flat side surfaces of the optical members 22 can be processed in any direction during the process of forming the reflective layers 32 on the optical members 22 and that the reflective layers 32, which have a flat shape, are easier to form than the reflective layers 3 and 31 described above. Another advantage is that, as in the first embodiment, the illumination device 300 allows effective and efficient illumination over a wide angular range, i.e., 180° or more, and is suitable for use with thin endoscopes.

Figure 8A:
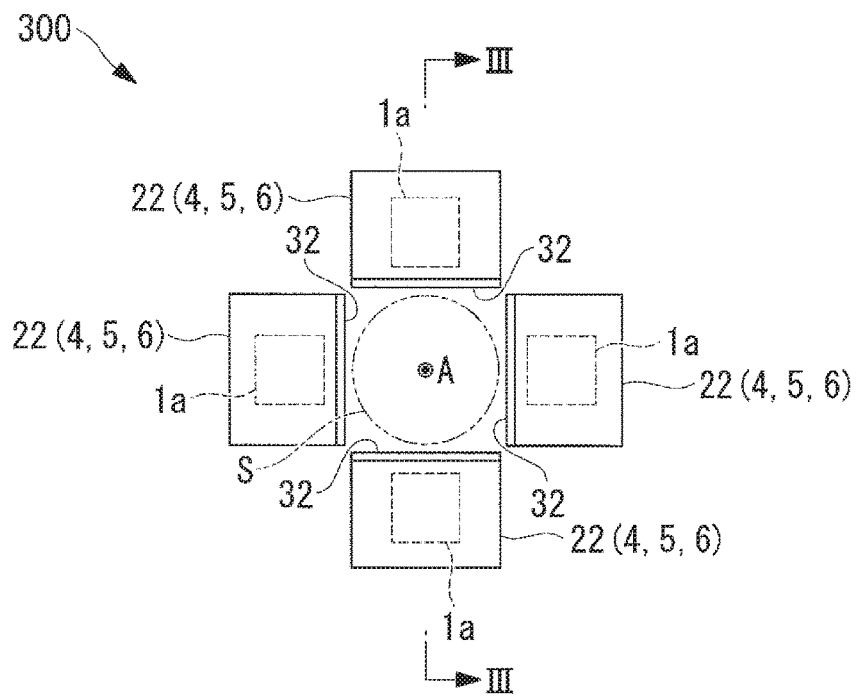
FIG. 8A is a front view of the illumination device, showing a modification of the shape of the optical member in FIGS. 7A and 7B.
Figure 8B:
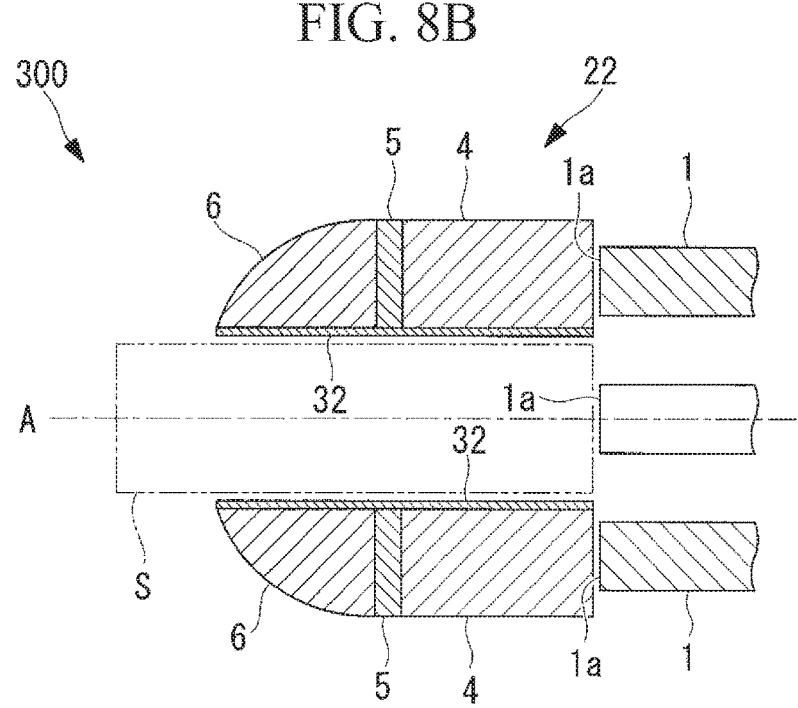
FIG. 8B is a longitudinal sectional view, taken along line III-III, of the illumination device in FIG. 8A.

In this embodiment, the optical members 22 may have any pillar shape with a flat side surface at the inner side in the radial direction. For example, as shown in FIGS. 8A and 8B, the optical members 22 may have a quadrangular prism shape with a rectangular transverse cross-section.

As shown in FIGS. 2 and 3, the output ends 1a of the light output units 1 in this embodiment may have shapes other than rectangles.

The optical members 22 in this embodiment may have a double-layer structure including the first light guide layer 4 and the diffusion layer 5.

The light guide layers 4 and 6 in this embodiment may have a sufficiently weaker diffusion effect on the illumination light than the diffusion layer 5 does.

The invention claimed is:

1. An illumination device comprising:
a light output unit having an output end that outputs illumination light;
an optical member that is disposed in a circumferential direction centered on a predetermined axis and that receives the illumination light from the output end and outputs the illumination light from a surface thereof; and
a reflective layer that is provided adjacent to a surface of the optical member at an inner side in a radial direction and that reflects the illumination light outward in the radial direction,
wherein the optical member comprises, in order from one end in a direction along the predetermined axis, a light guide layer and a diffusion layer,
the light guide layer receives the illumination light from the output end in the direction along the predetermined axis and guides the illumination light,
the diffusion layer receives the illumination light from the light guide layer and guides the illumination light while diffusing the illumination light, and
the diffusion layer and the light guide layer are disposed so as to output at least a part of the illumination light diffused at the diffusion layer from a surface of the light guide layer.

2. The illumination device according to claim 1, wherein the output end is circular, oval, polygonal, or annular-sector-shaped.

3. The illumination device according to claim 2, wherein the optical member is a substantially cylindrical member having a cutout formed by removing, in a longitudinal direction, a portion extending in the circumferential direction.

4. The illumination device according to claim 3, wherein the optical member forms a plurality of components arranged in the circumferential direction centered on the predetermined axis, each of the components is a substantially horseshoe-shaped pillar member having a side surface curved about the predetermined axis at the inner side in the radial direction, and the reflective layer is provided on the curved side surface.

5. The illumination device according to claim 2, wherein the optical member forms a plurality of components arranged in the circumferential direction centered on the predetermined axis, each of the components is a pillar member having a flat side surface at the inner side in the radial direction, and the reflective layer is provided on the flat side surface.

6. The illumination device according to claim 2, wherein the optical member further comprises another light guide layer disposed on a side of the diffusion layer facing another end in the direction along the predetermined axis.

7. The illumination device according to claim 2, wherein the light guide layer has a weaker diffusion effect on the illumination light than the diffusion layer does.

8. The illumination device according to claim 2, wherein the optical member is ring-shaped.

9. The illumination device according to claim 1, wherein the optical member is a substantially cylindrical member having a cutout formed by removing, in a longitudinal direction, a portion extending in the circumferential direction.

10. The illumination device according to claim 9, wherein the optical member forms a plurality of components arranged in the circumferential direction centered on the predetermined axis, each of the components is a substantially horseshoe-shaped pillar member having a side surface curved about the predetermined axis at the inner side in the radial direction, and the reflective layer is provided on the curved side surface.

11. The illumination device according to claim 1, wherein the optical member forms a plurality of components arranged in the circumferential direction centered on the predetermined axis, each of the components is a pillar member having a flat side surface at the inner side in the radial direction, and the reflective layer is provided on the flat side surface.

12. The illumination device according to claim 1, wherein the optical member further comprises another light guide layer disposed on a side of the diffusion layer facing another end in the direction along the predetermined axis.

13. The illumination device according to claim 1, wherein the light guide layer has a weaker diffusion effect on the illumination light than the diffusion layer does.

14. The illumination device according to claim 1, wherein the optical member is ring-shaped.

15. An illumination device comprising:

a light output unit having an output end that outputs illumination light;

an optical member that is disposed in a circumferential direction centered on a predetermined axis and that receives the illumination light from the output end and outputs the illumination light from a surface thereof; and a reflective layer that is provided inside a surface of the optical member at an inner side in a radial direction and that reflects the illumination light outward in the radial direction, wherein the optical member comprises, in order from one end in a direction along the predetermined axis, a light guide layer and a diffusion layer, the light guide layer receives the illumination light from the output end in the direction along the predetermined axis and guides the illumination light, the diffusion layer receives the illumination light from the light guide layer and guides the illumination light while diffusing the illumination light, and the diffusion layer and the light guide layer are disposed so as to output at least a part of the illumination light diffused at the diffusion layer from a surface of the light guide layer.

* * * * *